United States Patent [19]

Lerner et al.

[11] Patent Number: 5,300,097

[45] Date of Patent: Apr. 5, 1994

[54] FIBER OPTIC PSORIASIS TREATMENT DEVICE

[76] Inventors: Ethan A. Lerner, 20 St. Paul St., Brookline, Mass. 02146; R. Rox Anderson, 7 Campbell Park, Somerville, Mass. 02144; Michael R. Lerner, 27 Jayne La., Hamden, Conn. 06514

[21] Appl. No.: 947,893

[22] Filed: Sep. 18, 1992

Related U.S. Application Data

[63] Continuation of Ser. No. 654,829, Feb. 13, 1991, abandoned.

[51] Int. Cl.⁵ ............................................. A61M 5/06
[52] U.S. Cl. ........................................ 607/93; 607/94
[58] Field of Search .................... 15/195, DIG. 15; 128/395–398, 393; 350/96.3, 96.10; 250/504, 86; 606/15, 16; 362/32; 174/177; 549/280

[56] References Cited

U.S. PATENT DOCUMENTS

| 2,034,388 | 3/1936 | Cemach | 174/177 |
|---|---|---|---|
| 2,397,757 | 4/1946 | Schwedersky | 128/395 |
| 3,261,978 | 7/1966 | Brenman | 250/86 |
| 3,712,984 | 1/1973 | Lienhard | 250/86 |
| 4,161,050 | 7/1979 | Sasaki et al. | 15/DIG. 15 |
| 4,385,344 | 5/1983 | Gonser | 362/32 |
| 4,475,261 | 10/1984 | Okumara | 15/195 |
| 4,558,700 | 12/1985 | Mutzhas | 128/395 |
| 4,915,474 | 4/1990 | Kleh et al. | 350/96.3 |
| 4,948,215 | 8/1990 | Friedman | 350/96.10 |
| 5,216,176 | 6/1993 | Heindel et al. | 549/280 |

FOREIGN PATENT DOCUMENTS

| 3336939 | 4/1985 | Fed. Rep. of Germany | 128/395 |
|---|---|---|---|
| 3419464 | 12/1985 | Fed. Rep. of Germany | 128/395 |
| 2034462 | 6/1980 | United Kingdom | 128/395 |

*Primary Examiner*—Mark S. Graham
*Attorney, Agent, or Firm*—Lappin & Kusmer

[57] ABSTRACT

Disclosed is a therapeutic device including an optical source including means for generating ultraviolet (UV) radiation, and a light delivery apparatus. The light delivery apparatus includes a body member and a plurality of optical fibers extending therefrom. Each of the optical fibers includes a proximal tip affixed to the body member, a distal tip at the end of the fiber opposite the proximal tip, and means for coupling the generated radiation from the proximal tips of the fibers through the fibers, and to the distal tips. The distal tips are characterized by a radius of curvature in the range 0.25 to 2.0 mm. The coupling means includes a flexible central core disposed within a flexible outer cladding. The central core has a diameter in the range of 0.1 mm to 1.0 mm, and the cladding has a refraction less than the index of refraction of the core.

11 Claims, 2 Drawing Sheets

FIBER OPTIC PSORIASIS TREATMENT DEVICE

This application is a continuation of application Ser. No. 07/654,829, filed Feb. 13, 1991, abandoned.

BACKGROUND OF THE INVENTION

This invention relates to treatments for inflammatory diseases of the skin, and more specifically to methods for devices and treating ultraviolet light-sensitive dermatoses.

Inflammatory diseases of the skin affect a large portion of the population resulting in significant morbidity. Psoriasis, for example, affects at least 1% of the population. This disease involves an abnormally fast rate of cell proliferation in the basal layer of the epidermis giving rise to red, scaly plaques and bleeding when traumatized (the "Auspitz sign"). Past methods of treatment of skin psoriasis include the application of tars, salicylic acid, steroids, ultraviolet light (phototherapy), and a combination of ultraviolet light, used in conjunction with photoactive compounds (photochemotherapy).

Photochemotherapy involves treatment with ultraviolet radiation of an affected area in combination with a topically or systemically applied medicament that sensitizes the skin to ultraviolet radiation (e.g., psoralen). Typically ultraviolet-A (UV-A) light (so-called long wave UV light) having wavelengths from 310 to 440 nm is used for this purpose. Unfortunately, successful treatment requires that UV radiation must be applied until an erythema (sunburn) is created. In some cases, the eyes of patients systemic undergoing psoralen and topical UV treatment may be sensitized to sunlight for several hours after treatment. In addition, some patients find the medicament difficult to tolerate. Furthermore, this therapy requires 20-25 radiation sessions which result in darkening of the pigmentation of the skin. In addition, treatment of scalp psoriasis in particular has been limited by two other problems. First, patients are reluctant to apply medications regularly which must remain on their scalps for hours at a time. Second, light from conventional treatment devices does not effectively penetrate hair covering the scalp.

Phototherapy involves simply UV irradiation of the affected area. For example, psoriasis has been treated with ultraviolet-B (UV-B) light having wavelengths from 290-320 nm. Other skin diseases which have been treated successfully with ultraviolet light include eczema, mycosis fungoides, and lichen planus. In addition, ultraviolet light may have a role in the treatment of seborrheic dermatitis.

Phototherapeutic methods have included the use of mercury vapor high pressure radiation devices and those UV sources having varying spectral distribution. For example, UV-B lamps such as devices which produce radiation from a metal halide or mercury vapor source and which filters the emitted UV light with colored glass have been used (see e.g., U.S. Pat. No. 4,558,700). These devices emit UV in the range of 270-365 nm (mostly 270-315 nm), and cause erythema. Devices which emit wavelengths of 320-330 nm and greater have also been used for so-called super-high-intensive phototherapy (SHIP).

There is one prior art device that is adapted to deliver UV radiation to the scalp. That device is a hair brush for purportedly promoting the healthy flow of blood to the glands and roots of hair, and for promoting vitamin D production. The hair brush has an internal UV radiation source and UV radiation-transmitting bristles of a material other than a fiber optic material (Schwedersky, U.S. Pat. No. 2,397,757). Because the bristles of this device are rigid and pointed, its use on psoriasis-affected skin heightens the incidence of the Auspitz sign, and thus is contra-indicated for treatment of psoriasis.

Therefore, a need exists for a simple device and method useful for treating affected areas of the skin, particularly those hair-covered regions such as the scalp.

Accordingly, it is an object of this invention to provide a therapeutic device for the delivery of UV irradiation directly to an area of the body afflicted with psoriasis or other related dermatoses.

It is another object of the invention to provide a therapeutic device for the efficient delivery of UV light to an affected area with reduced specular reflection at the site of delivery.

Yet another object is to provide a method of treating psoriasis and related dermatoses which is easy to administer, rapid, and which minimizes unpleasant side effects such as erythema, pigmentation darkening, and the Auspitz sign.

An additional object of the invention is to provide a method of treating psoriasis which minimizes the therapeutic sessions required to result in relatively rapid healing.

These and other objects of the invention will be apparent from the drawing description, and claims that follow.

SUMMARY OF THE INVENTION

The present invention includes novel therapy devices for effective treatment of inflammatory dermatoses such as psoriasis. These devices comprise an optical source including means for generating ultraviolet (UV) light (radiation) in a predetermined spectral range, and a light delivery apparatus.

The optical source is preferably a tungsten or mercury discharge lamp, fluorescent bulb, or an excimer laser, such as one tuned to about 308-351 nm. A preferred embodiment includes a mercury or high intensity tungsten halogen lamp which is filtered to provide UV-B radiation of about 290-320 nm or UV-A radiation longer than about 310 nm. Embodiments including optical sources delivering UV-B irradiance of about 1-10 mW/cm$^2$ or delivering UV-A irradiance of about 30-1000 mW/cm$^2$ are most preferred.

The light delivery apparatus includes a body member and a plurality of optical fibers extending therefrom. The optical fibers are adapted to couple the light generated at the optical source from the proximal tips of the optical fibers, through the fibers, and to their distal tips. Each fiber has a proximal tip affixed to the body member and a distal tip at the end opposite the proximal tip. The distal tips of the fibers are characterized by a radius of curvature in the range 0.5-3 mm. The tip sphere at the distal end of the fiber may be composed of the same material as the fiber core, such as fused silica. In addition, each of the fibers has a flexible central core disposed within an outer cladding of lower refractive index. It preferably includes fused silicas, plastic, or glass. A preferred embodiment includes fibers having a core of fused silica with an index of refraction ($n_d$) of about 1.46.

The invention further includes methods of treating inflammatory dermatoses using the UV source and delivery device described above. The method includes contacting a region of the body afflicted with a dermatosis with the distal tips of the device such that UV light emanating therefrom is incident on the contacted region. Preferably, the contacting step includes contacting the body region with delivered UV-B irradiance of about 1-10 milliwatts per square centimeter (mW/cm$^2$) or with delivered UV-A irradiance of about 30-1000 mW/cm$^2$.

In some embodiments, the method includes the additional step of, prior to the contacting step, applying a medicant or lubricant to the region to be treated. Useful medicaments include psoralen, 8-methoxypsoralen (8-MOP) and trimethylpsoralen (TMP). Useful lubricants include many types of Oils, emulsions, and lotions. Such lubricants have an index of refraction closer to both that of the fiber core and the skin, than does air. This provides effective optical coupling between the fibers and the skin, and additionally reduces physical trauma. Preferably, pre-treatment with the lubricant reduces the specular reflection from the area to be treated. Specular reflection is undesirable as it reduces the amount of UV available to affect a treated area. In one embodiment, the preferred refractive index of lubricant is 1.55, the refractive index of skin. Other embodiments of the method of the invention include 8-MOP pre-treatment, and preferably include the application of about 0.001-0.1% of this medicament to the region to be treated.

DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
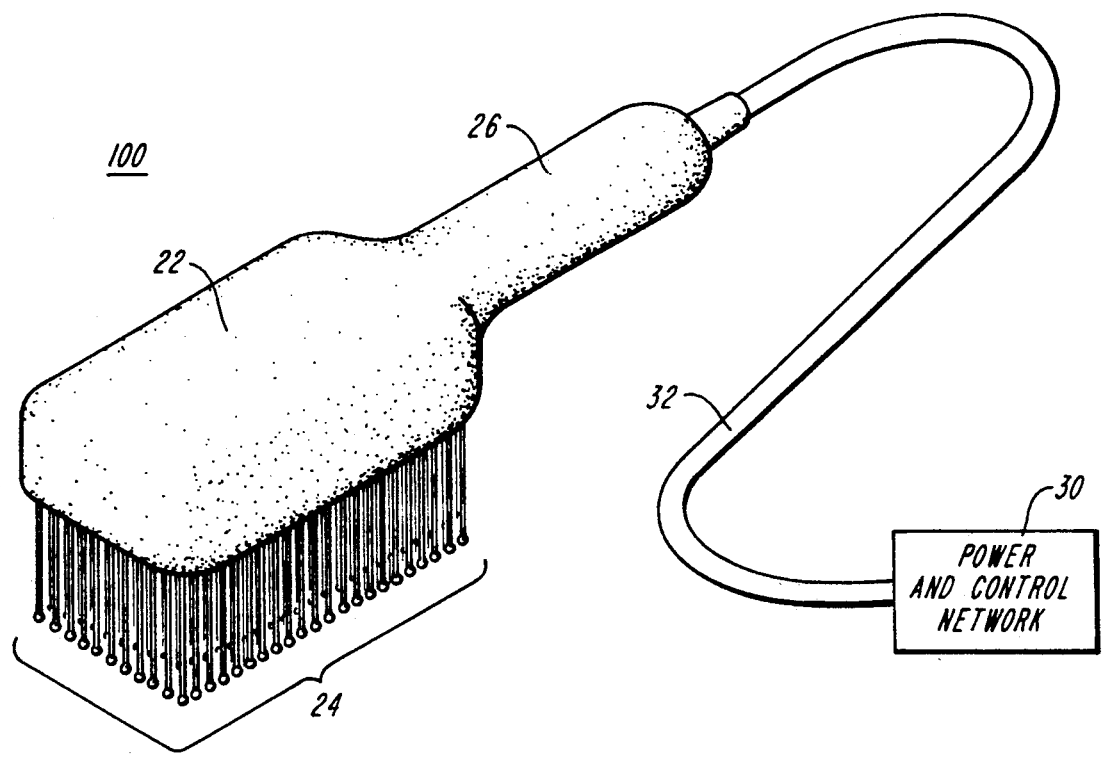
FIG. 1 is a perspective view showing an exemplary therapeutic device of the invention.

Therapeutic device 100 embodying the invention is shown in FIG. 1, and includes a light delivery apparatus including body member 22 and a plurality of optical fibers 24 extending therefrom. Body member 22 further includes a manual positioning device which, in the illustrated embodiment, is a handle 26. The body member 22 encloses an internal light source (shown in FIG. 2), which is powered by a power and control network 30 coupled by power cable 32.

Figure 2:
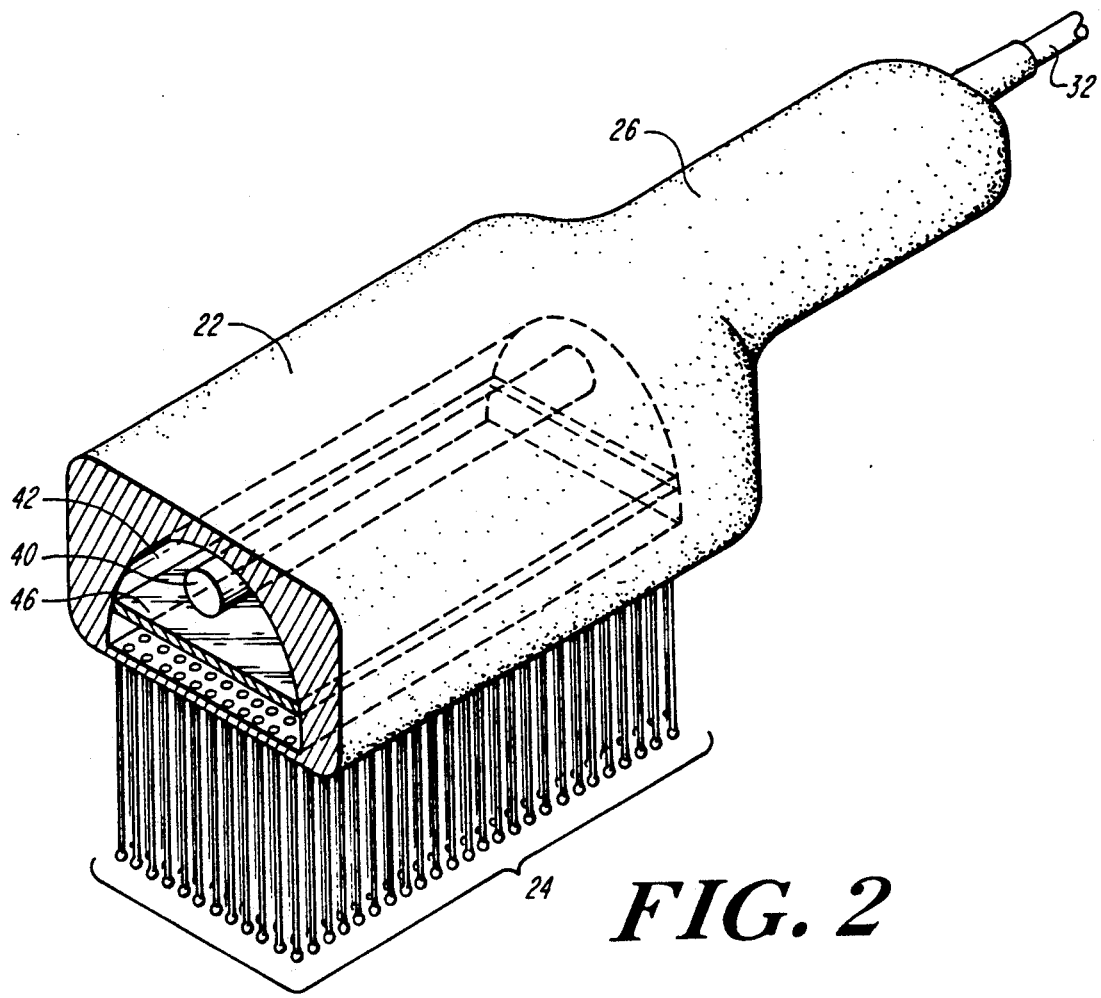
FIG. 2 is a detailed view of the embodiment of FIG. 1.

As shown in detail in FIG. 2, body member 22 is a substantially rectangular cross section body. That body is partially hollow and houses an elongated optical source 40 within hemi-elliptical reflector cavity 42. The optical fibers 24 extend from their proximal ends which are affixed to the open side of cavity 42. Preferably, body member 22 has substantially no UV-transferring abilities, and is formed of a molded resinous material, such as plastic, rubber, and the like. In some embodiments power source and control module 30 provides power via cable 32 through body member 22 to the optical source 10. Of course, body member 22 may instead include on-board batteries as a power source. Cavity 42 is preferably lined with an optically reflective material, for example, aluminum, electroformed or dichroic-coated glass, or silica, to minimize transmissional loss from optical source 10. Optical source 10 depicted in FIG. 2 is a fluorescent bulb 40. However, in accordance with the invention, optical source 10 alternatively may be a metal halide discharge lamp such as a mercury or high intensity tungsten lamp, or may be an exciser laser.

Positioned distally in front of optical source 10 within body member 22 is filter 46, which limits the wavelength of UV light reaching the proximal ends of fibers 24. Of course, more than one filter 16 can be positioned within body member 22 in close proximity to source 10.

Figures 3A, 3B:
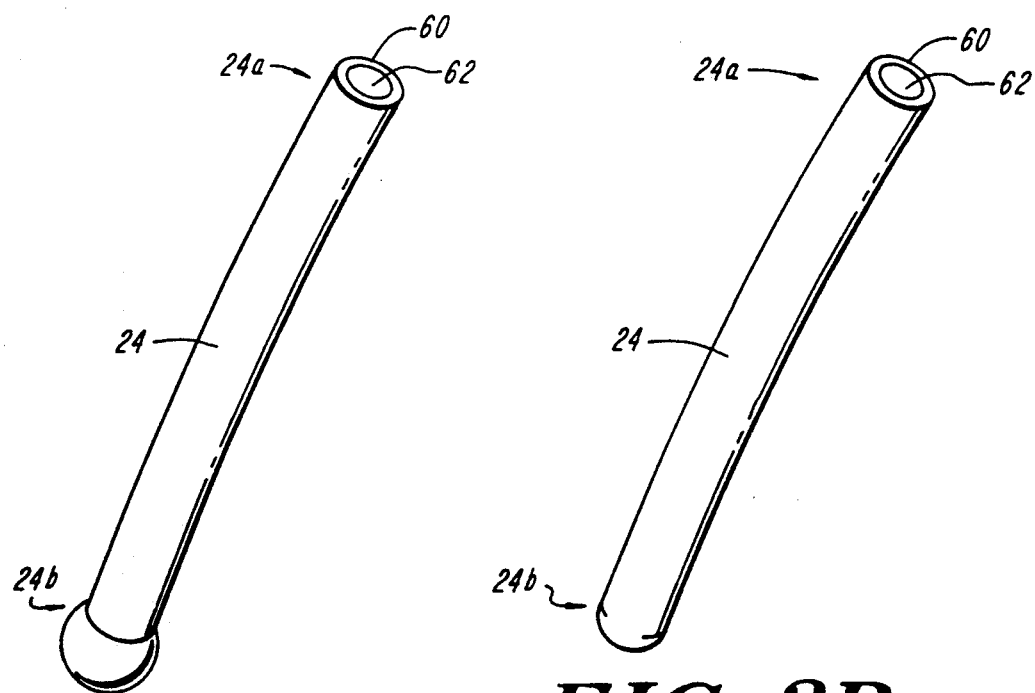
FIGS. 3A and 3B show detailed perspective views of exemplary fibers of the device of FIG. 1.

Two alternative forms for the individual optical fibers 24 are shown in FIGS. 3A and 3B. Each fiber is adapted for fixture to body member 22 at its proximal end 24a. Proximal tips 24a of fibers 24 may be embedded as individual elements within body member 22, or alternatively, may be adhered to the edges of voids formed body member 22 which are contiguous with cavity 42. Each of fibers 24 includes a central core 60 having a diameter in the range of 0.1-2 mm, and an outer cladding 62. Distal tips 24b of fibers 24 are spherical segments. In the embodiment of FIG. 3A, those tips have a UV light transmitting spherical element 64, while in the embodiment of FIG. 3B, the ends of the fiber 24 is rounded. The distal tip have a radius of curvature in the range of about 0.25-2.0 mm, to ensure that minimal damage is done to the skin during use. They should be smooth and small enough to easily be moved through the hair in brush-like fashion. Central core 60 is composed of a material which is capable of transmitting UV irradiation, such as fused silica, plastic, or glass. Outer cladding 22 is preferably formed from similar materials, but of lower refractive index.

Fibers 24 may be arranged in linear or rectangular arrays, or positioned in particular patterns as dictated by the geometry of the region-to-be-treated and which facilitates uniform dosimetry during use. Movement of the fiber arrays allows a selected area to be treated completely. The length of fibers 24 may also be variable for the same reason. For example, the device may be in the shape of a conventional handheld hair drying unit, where various groups of the UV illumination to fibers could be turned on or off in so as to treat large or limited areas of the scalp at the same time.

The therapeutic device described above can be easily used to treat inflammatory dermatoses affecting body regions covered by hair, such as the scalp. Fibers 24 can be positioned so that the distal tips 24b are pressed gently through such encumberances to contact the scalp during use. The blunting or rounding of distal tips 64 help to prevent development of the Auspitz sign during normal use.

Fibers 24 are hardy and ideally are autoclavable or able to be gas sterilized. In one embodiment the array of fibers can be interchangeable and replaceable.

Figure 4A:
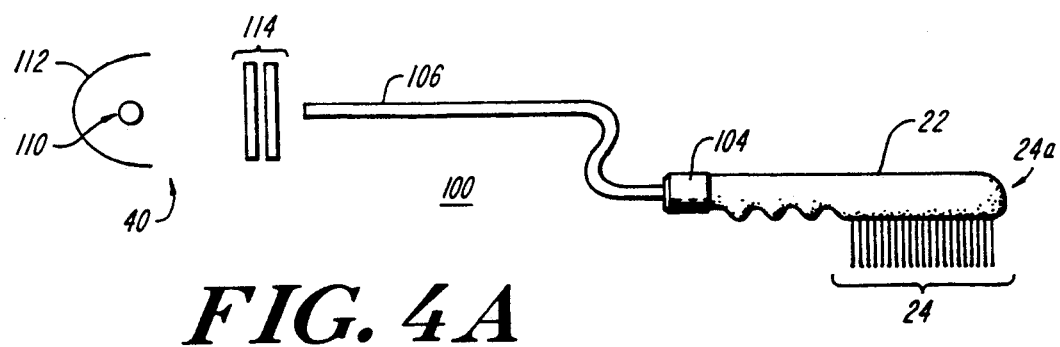
FIGS. 4A and 4B illustrate alternative embodiments of the invention.
Figure 4B:
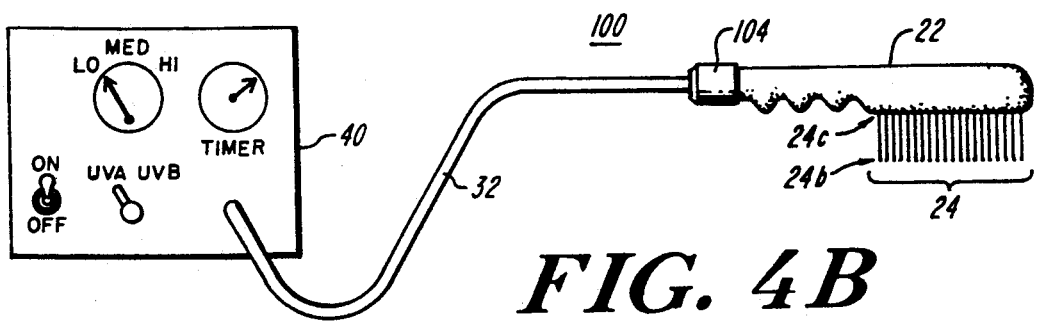

FIGS. 4A and 4B show alternative forms of the invention. In those figures, elements having corresponding elements in the embodiment of FIG. 1 are drawn with the same reference designations. In FIG. 4A, a "brush" device 102 includes a body member 22 from which a plurality of optical fibers 24 extend. The proximal ends 24a of fibers 24 extend via an optical coupler 104 and a UV transmitting flexible fluid light pipe, or fiber optical bundle 106 to a remote UV source 40. In this embodiment, the source 40 includes a tungsten-halogen, mercury or other UV source 110, a dichroic reflector 112, and optical filter 114.

In FIG. 4B, a configuration is shown which is similar to that in FIG. 4A, but where the source 40 has operator controls for selectively adjusting the duration, intensity, and spectral range of the UV radiation that is transmitted to the fibers 24.

The advantage of this device is that areas of the skin, such as the scalp, which were previously difficult and time consuming to treat, may now be easily treated. Also, localized areas of the skin may be treated without exposing the entire body to 8-MOP and/or to UV light.

Preferred embodiments of the method of treating an inflammatory dermatosis using the aforementioned device are as follows.

For UV-B phototherapeutic treatment, simple application while gently combing through the hair for prescribed times necessary is acceptable, beginning with approximately one minimum erythema dose (MED) during the first treatment. Subsequent treatment times would increase if needed and as tolerated by the skin.

Natural skin oils, water, or light lubricants applied to the scalp beneficially modify the optics of psoriatic skin, further reduce trauma, and provide good index matching to silica fibers.

For UV-A photochemotherapy, the skin would be pretreated by topical application of a solution containing 0.001–0.1% 8-MOP or some other medicaments for approximately 5 minutes, followed by washing out unadhered 8-MOP. The involved area of the skin subsequently would be exposed to the illuminated fiber optic array for a length of time corresponding to one MED during the first treatment. Of course, treatment times would depend upon skin type, the disease being treated, and the intensity of light reaching the skin. As with phototherapeutic use, subsequent treatment times would increase if needed and as tolerated by the skin.

The delivery of UV radiation into the skin via direct contact with a UV-transmitting optical fiber is more efficient than through air, due to refractive index mismatching between the skin ($n_d = 1.55$) and air ($n_d = 1.00$). By directly contacting the scalp with the preferred fiber optic core material, fused silica ($n_d = 1.46$), specular reflection at the scalp surface is greatly reduced, especially when a lubricant or topical application of psoralen-containing solution is present. The amount of such specular reflection varies mainly with the square of the difference in psoriasis, there is poor formation of the outermost skin layer. Thus, coupling of UV light into the psoriasis skin is much more efficient with direct contact between the fiber optic source and skin, in the presence of a lubricant or topical solution.

In practice, the delivered exposure dose (fluence) needs to be controlled to within about 40% absolute. Both short-term and long-term output stability, including solarization of spectral filters or windows, are considerations affecting dosimetry. If the source output is stable (e.g., less than 10% variation of UV irradiance) after a short warmup period, over the duration of one treatment (typically tens of minutes), then a timer type of device to control delivered dose based on a measured irradiance is appropriate. If the output is unstable, an integrating dosimeter is required. The ideal system would be stable, might require the user to point the output onto a detector which measured irradiance appropriately, then enter the desired dose in $J/cm^2$.

Of course other areas of the skin such as the nails could also be treated as described above.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A kit for the treatment of psoriasis comprising:
   A. a therapeutic device including:
      an optical source including means for generating ultraviolet (UV) radiation; and
      a light delivery apparatus including a body member and a plurality of optical fibers extending therefrom, each of said fibers including:
      a proximal tip affixed to said body member;
      a distal tip at the end of said fiber opposite said proximal tip, wherein the butt end of substantially all of said distal tips are characterized by a radius of curvature in the range of 0.25 to 2.0 mm;
      means for coupling said generated radiation from said proximal tips of said optical fibers through said fibers, and to said distal tips, said coupling means including a flexible central core disposed within a flexible outer cladding, said central core having a diameter in the range of 0.1 mm to 1.0 mm, and said cladding having a refraction less than the index of refraction of said core, and
   B. a lubricant having an index of refraction intermediate of the index of refraction of said core and a predetermined reference value wherein said lubricant has an index of refraction intermediate of the index of refraction of said core and a reference value of about 1.55.

2. A kit according to claim 1 wherein said lubricant is selected from the group consisting of 8-methoxypsoralen (8-MOP), trimethylpsoralen (TMP) in a lubricant base or lotion.

3. The device of claim 1 wherein said optical source comprises means for generating UV-A radiation in the spectral range of about 310 to 400 nm.

4. The device of claim 1 wherein said optical source comprises means for generating UV-B radiation in the spectral range of about 290 to 320 nm.

5. The device of claim 1 wherein said optical source is adapted to generate UV-A radiation of about 30–1000 $mW/cm^2$ at said distal tips.

6. The device of claim 1 wherein said optical source is adapted to generate UV-B radiation of about 1–10 $mW/cm^2$ at said distal tips.

7. The device of claim 1 wherein said optical source is selected from the group consisting of mercury discharge lamps, high intensity tungsten discharge lamps, fluorescent bulbs, and excimer lasers.

8. The device of claim 7 wherein said optical source is an excimer laser tuned to about 308 to 351 nm.

9. The device of claim 1 wherein said core is comprised of a material selected from the group consisting of fused silicas, plastic, and glass.

10. The device of claim 9 wherein said core comprises fused silica.

11. The device of claim 10 wherein the index of refraction of said core is about 1.46.

* * * * *